United States Patent
Shetty

(10) Patent No.: US 8,193,417 B2
(45) Date of Patent: Jun. 5, 2012

(54) CUCUMBER LINE APD147-5002GY

(75) Inventor: Nischit Shetty, Tifton, GA (US)

(73) Assignee: Seminis Vegetable Seeds, Inc., Woodland, CA (US)

( * ) Notice: Subject to any disclaimer, the term of this patent is extended or adjusted under 35 U.S.C. 154(b) by 279 days.

(21) Appl. No.: 12/014,643

(22) Filed: Jan. 15, 2008

(65) Prior Publication Data

US 2008/0229440 A1    Sep. 18, 2008

Related U.S. Application Data

(60) Provisional application No. 60/885,566, filed on Jan. 18, 2007.

(51) Int. Cl.
- *A01H 1/00* (2006.01)
- *A01H 5/00* (2006.01)
- *A01H 5/10* (2006.01)
- *C12N 15/82* (2006.01)
- *C12N 5/04* (2006.01)
- *C12Q 1/68* (2006.01)

(52) U.S. Cl. ......... 800/307; 435/410; 435/6.1; 800/260; 800/278

(58) Field of Classification Search ......... None
See application file for complete search history.

(56) References Cited

U.S. PATENT DOCUMENTS

| 5,492,827 | A | 2/1996 | Dirks | 435/240.45 |
| 6,765,130 | B2 * | 7/2004 | Taurick | 800/307 |
| 2009/0064355 | A1 | 3/2009 | Shetty et al. | 800/307 |
| 2009/0210964 | A1 | 8/2009 | Shetty et al. | 800/307 |
| 2010/0251413 | A1 * | 9/2010 | Shetty et al. | 800/265 |

OTHER PUBLICATIONS

Wehner (2001, http://cuke.hort.ncsu.edu/cucurbit/cuke/cktrials/ckrpt01pk3.html).*
Sarreb et al., "Comparison of triploid and diploid cucumber in long-term liquid cultures," *Plant Cell, Tissue and Organ Culture*, 71:231-235, 2002.
U.S. PVP Application No. for *Cucumis sativaus* L. Variety APD147-5002GY, dated Nov. 9, 2007.
U.S. Appl. No. 12/197,824, filed Aug. 25, 2008, Shetty.
U.S. Application for Plant Variety Protection for Cucumber Variety (*Cucumis sativus* L.) APD147-5007Gy, filed Nov. 13, 2007.
Request for Information under 37 CFR § 1.105 regarding U.S. Appl. No. 12/197,824, dated Sep. 30, 2010.
Response to Request for Information under 37 CFR § 1.105 regarding U.S. Appl. No. 12/197,824, dated Jan. 13, 2011.
Official Action concerning U.S. Appl. No. 12/197,824 dated Sep. 15, 2011.

* cited by examiner

*Primary Examiner* — Anne Kubelik
(74) *Attorney, Agent, or Firm* — SNR Denton US LLP; Alissa Eagle Esq.

(57) ABSTRACT

The invention provides seed and plants of the cucumber line designated APD147-5002Gy. The invention thus relates to the plants, seeds and tissue cultures of cucumber line APD147-5002Gy, and to methods for producing a cucumber plant produced by crossing a plant of cucumber line APD147-5002Gy with itself or with another cucumber plant, such as a plant of another line. The invention further relates to seeds and plants produced by such crossing. The invention further relates to parts of a plant of cucumber line APD147-5002Gy, including the fruit and gametes of such plants.

25 Claims, No Drawings

CUCUMBER LINE APD147-5002GY

This application claims the priority of U.S. Provisional Application Ser. No. 60/885,566, filed Jan. 18, 2007, the entire disclosure of which is specifically incorporated herein by reference.

BACKGROUND OF THE INVENTION

1. Field of the Invention

The present invention relates to the field of plant breeding and, more specifically, to the development of cucumber line APD147-5002Gy.

2. Description of Related Art

The goal of vegetable breeding is to combine various desirable traits in a single variety/hybrid. Such desirable traits may include, for example, greater yield, resistance to insects or pests, tolerance to heat and drought, better agronomic quality, higher nutritional value, growth rate and fruit properties.

Breeding techniques take advantage of a plant's method of pollination. There are two general methods of pollination: a plant self-pollinates if pollen from one flower is transferred to the same or another flower of the same plant or plant variety. A plant cross-pollinates if pollen comes to it from a flower on a different plant.

Plants that have been self-pollinated and selected for type over many generations become homozygous at almost all gene loci and produce a uniform population of true breeding progeny, a homozygous plant. A cross between two such homozygous plants of different varieties produces a uniform population of hybrid plants that are heterozygous for many gene loci. Conversely, a cross of two plants each heterozygous at a number of loci produces a population of hybrid plants that differ genetically and are not uniform. The resulting non-uniformity makes performance unpredictable.

The development of uniform varieties requires the development of homozygous inbred plants, the crossing of these inbred plants, and the evaluation of the crosses. Pedigree breeding and recurrent selection are examples of breeding methods that have been used to develop inbred plants from breeding populations. Those breeding methods combine the genetic backgrounds from two or more plants or various other broad-based sources into breeding pools from which new lines are developed by selfing and selection of desired phenotypes. The new lines are evaluated to determine which of those have commercial potential.

One crop species which has been subject to such breeding programs and is of particular value is the cucumber. Cucumber (*Cucumis sativus* L.) is naturally a diploid (2n=14) outcrossing species originating in Asia or Africa, although haploid, doubled-haploid (U.S. Pat. No. 5,492,827), and triploid (Sarreb et al., 2002) types have been developed. The two main types of cucumber fruit grown commercially today in the United States are fresh market (slicing) type and the processing (pickling) type. Varieties and production methods are typically adapted to the end use. Slicing cucumbers are often longer, larger and have darker and thicker skin, whereas pickling/processing cucumbers have a shorter fruit, thinner skin with interior flesh that make them more amenable to pickling. Seedless varieties are generally preferable for both fresh market and for pickling as developing and large seeds are not palatable.

Until the 1960s cucumbers were normally monoecious, e.g., having separate male and female flowers on the same plant. Perfect flowers are uncommon in cucumbers, and staminate flowers are typically single and/or in clusters. Pistillate flowers may be solitary or in clusters and are borne on stout peduncles. Gynoecious cucumber plants have now been identified in which flowers are exclusively pistillate. These plants are generally higher yielding, due at least in part to the presence of higher numbers of female flowers. However, growth of gynoecious hybrid plants in the field has historically required the addition of plants of a monoecious line or variety (~10-15%) to ensure availability of pollen and setting of fruit with seed. Honey bees are the most commonly used insects to pollinate cucumbers in the open field.

Cucumber plants that set fruit parthenocarpically (without pollination and fertilization) have more recently been available. These plants produce seedless fruit unless pollinated. Growth of parthenocarpic varieties is beneficial in that setting of fruit on these cultivars does not produce an inhibiting effect on plant growth, unlike the case of fertilized, seeded fruit. The seedless varieties are usually higher yielding and of higher quality due to the lack of seeds. Growth of these plants requires isolation from seeded cucumbers to avoid pollination and subsequent seeded fruit.

Most of the cucumbers currently used which are processed to pickles and pickle products in the United States are seeded hybrid varieties. Hybrid varieties offer the advantages of easy combination of dominant and recessive traits, such as disease resistance, from a set of inbred parents, as well as careful control of parentage. The production of $F_1$ hybrid cucumber seeds from a pollen parent bearing only male flowers has been reported (U.S. Pat. No. 4,822,949).

Many different cucumber cultivars have been produced, and cucumber breeding efforts have been underway in many parts of the world (see, e.g. U.S. Pat. No. 6,765,130). Some breeding objectives include varying the color, texture and flavor of the fruit. Minimizing the occurrence of bitterness in cucumbers is one such example. Other objectives include optimizing flesh thickness, solid content (% dry matter), and sugar content. Also, breeding programs have focused on developing plants with earlier fruit maturity, more restricted vine growth, improved disease resistance or tolerance, and improved adaptability to environmental conditions.

Advances in biotechnology have resulted in genetically engineered cucumber plants with improved traits. For example, cucumbers resistant to CMV have been developed by expression of CMV protein coat genes (see e.g. U.S. Pat. Nos. 6,342,655, 6,127,601, 5,623,066, 5,349,128). Transgenic plants exhibiting, for example, other viral resistance traits or high levels of superoxide dismutase have also been reported (U.S. Pat. Nos. 6,015,942; 6,084,152).

While breeding efforts to date have provided a number of useful cucumber lines with beneficial traits, there remains a great need in the art for new lines with further improved traits. Such plants would benefit farmers and consumers alike by improving crop yields and/or quality.

SUMMARY OF THE INVENTION

In one aspect, the invention provides a cucumber plant of the line designated APD147-5002Gy. Also provided are cucumber plants having all the physiological and morphological characteristics of the cucumber line designated APD147-5002Gy. Parts of the cucumber plant of the present invention are also provided, for example, including pollen, an ovule, a fruit, and a cell of the plant.

The invention also concerns seed of cucumber line APD147-5002Gy. The cucumber seed of the invention may be provided as an essentially homogeneous population of cucumber seed of the line designated APD147-5002Gy. Essentially homogeneous populations of seed are generally free from substantial numbers of other seed. Therefore, seed of line APD147-5002Gy may be defined as forming at least about 97% of the total seed, including at least about 98%, 99%, or more of the seed. The population of cucumber seed may be particularly defined as being essentially free from hybrid seed. The seed population may be separately grown to provide an essentially homogeneous population of cucumber plants designated APD147-5002Gy.

In another aspect of the invention, a plant of cucumber line APD147-5002Gy comprising an added heritable trait is provided. The heritable trait may comprise a genetic locus that is, for example, a dominant or recessive allele. In one embodiment of the invention, a plant of cucumber line APD147-5002Gy is defined as comprising a single locus conversion. In specific embodiments of the invention, an added genetic locus confers one or more traits such as, for example, herbicide tolerance, insect resistance, disease resistance, and modified carbohydrate metabolism. In further embodiments, the trait may be conferred by a naturally occurring gene introduced into the genome of the line by backcrossing, a natural or induced mutation, or a transgene introduced through genetic transformation techniques into the plant or a progenitor of any previous generation thereof. When introduced through transformation, a genetic locus may comprise one or more genes integrated at a single chromosomal location.

In another aspect of the invention, a tissue culture of regenerable cells of a plant of line APD147-5002Gy is provided. The tissue culture will preferably be capable of regenerating plants capable of expressing all of the physiological and morphological characteristics of the line, and of regenerating plants having substantially the same genotype as other plants of the line. Examples of some of the physiological and morphological characteristics of the line APD147-5002Gy include those traits set forth in the tables herein. The regenerable cells in such tissue cultures may be derived, for example, from embryos, meristems, cotyledons, pollen, leaves, anthers, roots, root tips, pistil, flower, seed and stalks. Still further, the present invention provides cucumber plants regenerated from a tissue culture of the invention, the plants having all the physiological and morphological characteristics of line APD147-5002Gy.

In yet another aspect of the invention, processes are provided for producing cucumber seeds, plants and fruit, which processes generally comprise crossing a first parent cucumber plant with a second parent cucumber plant, wherein at least one of the first or second parent cucumber plants is a plant of the line designated APD147-5002Gy. These processes may be further exemplified as processes for preparing hybrid cucumber seed or plants, wherein a first cucumber plant is crossed with a second cucumber plant of a different, distinct line to provide a hybrid that has, as one of its parents, the cucumber plant line APD147-5002Gy. In these processes, crossing will result in the production of seed. The seed production occurs regardless of whether the seed is collected or not.

In one embodiment of the invention, the first step in "crossing" comprises planting seeds of a first and second parent cucumber plant, often in proximity so that pollination will occur for example, mediated by insect vectors. Alternatively, pollen can be transferred manually. Where the plant is self-pollinated, pollination may occur without the need for direct human intervention other than plant cultivation.

A second step may comprise cultivating or growing the seeds of first and second parent cucumber plants into plants that bear flowers. A third step may comprise preventing self-pollination of the plants, such as by emasculating the male portions of flowers, (i.e., treating or manipulating the flowers to produce an emasculated parent cucumber plant). Self-incompatibility systems may also be used in some hybrid crops for the same purpose. Self-incompatible plants still shed viable pollen and can pollinate plants of other varieties but are incapable of pollinating themselves or other plants of the same line.

A fourth step for a hybrid cross may comprise cross-pollination between the first and second parent cucumber plants. Yet another step comprises harvesting the seeds from at least one of the parent cucumber plants. The harvested seed can be grown to produce a cucumber plant or hybrid cucumber plant.

The present invention also provides the cucumber seeds and plants produced by a process that comprises crossing a first parent cucumber plant with a second parent cucumber plant, wherein at least one of the first or second parent cucumber plants is a plant of the line designated APD147-5002Gy. In one embodiment of the invention, cucumber seed and plants produced by the process are first generation ($F_1$) hybrid cucumber seed and plants produced by crossing a plant in accordance with the invention with another, distinct plant. The present invention further contemplates plant parts of such an $F_1$ hybrid cucumber plant, and methods of use thereof. Therefore, certain exemplary embodiments of the invention provide an $F_1$ hybrid cucumber plant and seed thereof.

In still yet another aspect of the invention, the genetic complement of the cucumber plant line designated APD147-5002Gy is provided. The phrase "genetic complement" is used to refer to the aggregate of nucleotide sequences, the expression of which sequences defines the phenotype of, in the present case, a cucumber plant, or a cell or tissue of that plant. A genetic complement thus represents the genetic makeup of a cell, tissue or plant, and a hybrid genetic complement represents the genetic make up of a hybrid cell, tissue or plant. The invention thus provides cucumber plant cells that have a genetic complement in accordance with the cucumber plant cells disclosed herein, and plants, seeds and plants containing such cells.

Plant genetic complements may be assessed by genetic marker profiles, and by the expression of phenotypic traits that are characteristic of the expression of the genetic complement, e.g., isozyme typing profiles. It is understood that line APD147-5002Gy could be identified by any of the many well known techniques including, but not limited to, Simple Sequence Length Polymorphisms (SSLPs) (Williams et al., 1990), Randomly Amplified Polymorphic DNAs (RAPDs), DNA Amplification Fingerprinting (DAF), Sequence Characterized Amplified Regions (SCARs), Arbitrary Primed Polymerase Chain Reaction (AP-PCR), Amplified Fragment Length Polymorphisms (AFLPs) (EP 534 858, specifically incorporated herein by reference in its entirety), and Single Nucleotide Polymorphisms (SNPs) (Wang et al., 1998).

In still yet another aspect, the present invention provides hybrid genetic complements, as represented by cucumber plant cells, tissues, plants, and seeds, formed by the combination of a haploid genetic complement of a cucumber plant of the invention with a haploid genetic complement of a second cucumber plant, preferably, another, distinct cucumber plant. In another aspect, the present invention provides a cucumber plant regenerated from a tissue culture that comprises a hybrid genetic complement of this invention.

In still yet another aspect, the invention provides a plant of an inbred cucumber line that exhibits resistance to one or more of Angular leaf spot (*Pseudomonas lachrymans*, also known as *Pseudomonas syringae* pv. *lachrymans*), Anthracnose race 1 (*Colletotrichum orbiculare*), Cucumber Scab (*Cladosporium cucumerinum*), Downy mildew (*Pseudoperonospora cubensis*), Powdery Mildew (*Sphaerotheca fuliginea*) and Cucumber Mosaic Virus. In certain embodiments, the trait may be defined as controlled by genetic means for the expression of the trait found in cucumber line APD147-5002Gy.

In still yet another aspect, the invention provides a method of determining the genotype of a plant of cucumber line APD147-5002Gy comprising detecting in the genome of the plant at least a first polymorphism. The method may, in certain embodiments, comprise detecting a plurality of polymorphisms in the genome of the plant. The method may further comprise storing the results of the step of detecting the plurality of polymorphisms on a computer readable medium. The invention further provides a computer readable medium produced by such a method.

In still yet another aspect, the invention provides a method of producing a cucumber plant derived from the cucumber line APD147-5002Gy, the method comprising the steps of: (a) preparing a progeny plant derived from cucumber line APD147-5002Gy, wherein said preparing comprises crossing a plant of the cucumber line APD147-5002Gy with a second cucumber plant; (b) crossing the progeny plant with itself or a second plant to produce a seed of a progeny plant of a subsequent generation; (c) growing a progeny plant of a subsequent generation from said seed of a progeny plant of a subsequent generation and crossing the progeny plant of a subsequent generation with itself or a second plant; and repeating the steps for an additional 3-10 generations to produce a cucumber plant derived from cucumber line APD147-5002Gy. The plant derived from cucumber line APD147-5002Gy may be an inbred line the subsequent crossing steps may be defined as comprising sufficient inbreeding to produce the inbred line. In the method, it may be desirable to select particular plants resulting from step (c) for continued crossing according to steps (b) and (c). By selecting plants having one or more desirable traits, a cucumber plant derived from the cucumber line APD147-5002Gy is obtained which possesses some of the desirable traits of cucumber line APD147-5002Gy as well as potentially other selected traits.

In certain embodiments, the present invention provides a method of producing cucumber comprising: (a) cultivating a plant of cucumber line APD147-5002Gy to maturity and (b) obtaining at least a first cucumber from the plant.

These and other features and advantages of this invention are described in, or are apparent from, the following detailed description of various exemplary embodiments of the devices and methods according to this invention.

DETAILED DESCRIPTION OF THE INVENTION

The invention provides methods and compositions relating to plants, seeds and derivatives of cucumber line APD147-5002Gy. This line shows uniformity and stability within the limits of environmental influence for the traits described hereinafter. cucumber line APD147-5002Gy provides sufficient seed yield. By crossing with a distinct second plant, uniform F1 hybrid progeny can be obtained.

Line APD147-5002Gy exhibits a number of improved traits including resistance to one or more of Angular leaf spot (*Pseudomonas lachrymans*, also known as *Pseudomonas syringae* pv. *lachrymans*), Anthracnose race 1 (*Colletotrichum orbiculare*), Cucumber Scab (*Cladosporium cucumerinum*), Downy mildew (*Pseudopernospora cubensis*), Powdery Mildew (*Sphaerotheca fuliginea*) and Cucumber Mosaic Virus. The fruits of APD147-5002 Gy have a similar fruit shape, color, and spines to a seeded American pickling cucumber. The development of the line is discussed further below.

A. Origin and Breeding History of Cucumber Line APD147-5002Gy

Inbred line API147-5002Gy was developed from an initial single cross, made in Year 1, of two lines, designated 12530 and 12533. Line 12530 is an inbred pickling cucumber line with good fruit quality, fruit color, fruit shape, resistance to Angular leaf spot (*Pseudomonas lachrymans*, also known as *Pseudomonas syringae* pv. *lachrymans*), Anthracnose race 1 (*Colletotrichum orbiculare*), Cucumber Scab (*Cladosporium cucumerinum*), Powdery Mildew (*Sphaerotheca fuliginea*) and Cucumber Mosaic Virus and good adaptability to different growing conditions in North America and Mexico. Line 12533 is a parthenocarpic line with good adaptability in Europe.

After the initial cross was made, progeny were tested for parthenocarpy, gynoecy, plant habit, fruit quality, and resistance to Anthracnose, Angular leaf spot, Scab and Cucumber Mosaic Virus. The selected progeny were then self or sib-pollinated for inbred advancement in the field (plot number T96S-20792) during the spring of Year 2. Seeds of the resulting plants were then planted in the greenhouse (plot T96S-24017) during the summer of Year 2. Selections were made from the resulting plants for plant habit, fruit type and parthenocarpy. The selections were planted during the Fall of Year 2 in plot T96F-24217, selfed, and selections were made based on fruit quality, fruit color, parthenocarpy and plant habit (T96F-24217H2).

Selections from plot T96F-24217H2 were planted during the spring of Year 3 in plot T97S-20752. The plants were selfed and selections were made based on fruit quality, fruit color, parthenocarpy and plant habit.

Selections from plot T97S-20752 were planted during the Fall of Year 3 in plot T97F-27258; selections were made for fruit quality, fruit color and plant habit (T97F-27258B1).

Selections from plot T97F-27258B1 were planted in a greenhouse plot (designated T98S-31268) during the spring of Year 4. The plants were selfed and selections were made based on fruit quality, fruit color, parthenocarpy and plant habit (T98S-31268G2).

Selections from plot T98S-31268G2 were grown in the Fall of Year 4 in plot 36577 and were selected for fruit quality, fruit color, parthenocarpy and plant habit (T98F-36577A).

Selections from plot T98F-36577A were planted during the Fall of Year 5 in plot T99F-26705, and selections were made based on fruit quality, fruit color and plant habit (T99F-26705A2).

Selections from plot T99F-26705A2 were planted in a greenhouse plot (designated T00S-21374) during the spring of Year 6. The plants were selfed and selections were made based on fruit quality, fruit color, parthenocarpy and plant habit (T00S-21374K1).

Selections from plot T00S-21374K1 were planted in a greenhouse plot (designated T00F-29418) during the Fall of Year 6. The plants and were selfed and selections were made based on fruit quality, fruit color, parthenocarpy and plant habit (T00F-29418F1).

Selections from plot T00F-29418K1 were planted in greenhouse plot T01W-31878 during the winter of Year 7. The plants were selfed and selections were made for fruit quality, fruit color, parthenocarpy and plant habit (T01W-31878A1).

Selections from plot T01W-31878A1 were planted during the Fall of Year 7 in plot T01F-38008, and selections were made based on fruit quality, fruit color and plant habit (T01F-38008E2).

Selections from plot T01F-38008E2 were planted in a greenhouse plot (designated T02W-41539) during the Winter of Year 8. Resistant plants were selfed and selections were made based on fruit quality, fruit color, parthenocarpy and plant habit (T02W-41539D1).

Selections from plot T02W-41539D1 were planted in plot T02S-46912 during the Summer of Year 8 in the greenhouse and selfed, and the line was designated as APD147-5002Gy.

B. Physiological and Morphological Characteristics of Cucumber Line APD147-5002Gy In accordance with one aspect of the present invention, there is provided a plant having the physiological and morphological characteristics of cucumber line APD147-5002Gy. A description of the physiological and morphological characteristics of cucumber line APD147-5002Gy is presented below, in Table 1.

TABLE 1

Physiological and Morphological Characteristics of Line APD147-5002Gy

| CHARACTERISTIC | APD147-5002Gy |
| --- | --- |
| 1. Type | Cucumber |
|    Predominate Usage | Pickling |
|    Predominate Culture | Outdoor |
|    Area of Best Adaptation in USA | Most Areas |
| 2. Maturity | |
|    Days from Seeding to Market | 48 |
| 3. Plant | |
|    Habit | Vine |
|    Growth | Indeterminate |
|    Sex Expression | 100% gynoecious (Farbio, Sandra, Wilma) |
|    Number of female flowers per node | 1 to 3 (Hokus, Sandra) |
|    Flower Color | Yellow |
|    Flower Color (RHS Color Chart value) | 9A |
| 4. Stem | |
|    Main stem: measurements | 138 cm |
|    Number of Nodes from Cotyledon Leaves to Node Bearing the First Pistillate Flower | 1 |
|    Internode Length | 10.0 cm |
|    Stem Form | Grooved-Ridged |
|    Plant: total length of first 15 internodes | Short (Kora, Maran, Naf, Tagor) |
|    Plant: length of internodes of side shoots | Short |
| 5. Leaf | Mature Blade of Third Leaf |
|    Length | 184 mm |
|    Width | 168 mm |
|    Petiole Length | 8.5 cm |
|    Blistering | Weak (Pepinex 69, Rocket GS) |
|    Undulation of Margin | Weak (Pepinex 69, Rocket GS) |
|    Length of terminal lobe | Short (Komim) |
|    Width of terminal lobe | Medium |
|    Ratio length/width of terminal lobe | More than 1 (Riesenchal) |
| 6. Young Fruit | |
|    Type of vestiture | Prickles only (Tagor) |
|    Density of vestiture | Sparse (Tagor) |
|    Color of vestiture | White (Farbio, Levo, Rocket GS, Sandra) |
|    Size of warts | Small (Astrea, Breso, Donor, Uwy) |
|    Parthenocarpy | Present (Farbio, Rocket GS, Sandra, Wilma) |
|    Fruit: Length | Medium (Gemini) |
| 7. Fruit at Edible Maturity | |
|    Length | 14.0 cm |
|    Diameter at Medial | 5.0 cm |
|    Core diameter in relation to diameter of fruit | Large (Beth Alpha, Vert petit de Paris) |
|    Weight | 232 gm |
|    Skin Color/Mottling | Mottled or Speckled with yellow |
|    Predominant type of mottling | Small and round |
|    Intensity of mottling | Weak (Raider) |
|    Yellowish Blossom End Strips | Extend Less than 1/3 of the Fruit Length |
|    Predominant Color at Stem End | Dark Green |
|    Predominant Color at Stem End | RHS Color Chart value = 139A |
|    Predominant Color at Blossom End | Light Green |
|    Predominant Color at Blossom End | RHS Color Chart value = 144D |
|    Fruit Neck Shape | Not Necked |
|    Predominant shape of stem end at market stage | Acute (DeMassy, Maxor) |
|    Shape of calyx end at market stage | Acute (De Massy, Maxor, Pepinex 69) |
|    Fruit Tapering | Stem end tapered |
|    Stem End Cross Section | Circular |
|    Medial Cross Section | Triangular |
|    Blossom End Cross Section | Circular |
|    Ground color of skin at market stage | Green (Corona) |
|    Intensity of ground color of skin | medium |
|    Skin Thickness | Thick |
|    Skin Ribs | Absent/not ribbed (Marem, Riesenchal) |
|    Prominence of ribs | Weak (Donor, Rocket GS) |
|    Coloration of ribs compared to ground color | Equal |
|    Skin Toughness | Tough |
|    Skin Luster | Dull |
|    Spine Color | White |
|    Spine Quality | Coarse |
|    Spine Density | Few |
|    Warts | Present (Dumex) |

TABLE 1-continued

Physiological and Morphological Characteristics of Line APD147-5002Gy

| CHARACTERISTIC | APD147-5002Gy |
|---|---|
| Tubercles (Warts) | Few, Obscure |
| Stripes (ribs excluded) | Absent (Pepinex 69) |
| Length of stripes | Short (Astrea) |
| Length of peduncle | Medium (Aries, Femdan) |
| Thickness of peduncle | Medium (Dominant) |
| Ground color of skin at physiological ripening | Green |
| Time of development of female flowers (80% of plants with at least one female flower) | Medium |
| Cotyledon: bitterness | Absent |
| Flavor/bitterness at stem end | Absent/Bitterfree |
| 8. Fruit Seed at Harvest Maturity | |
| Length | 1.0 cm |
| Diameter at Medial | 0.4 cm |
| Color | Cream |
| Color (RHS Color Chart Value) | 161D |
| Color Pattern | Not Striped |
| Surface | Smooth |
| Netting | Slight or None |
| 9. Seeds | |
| No. per Fruit | 239 |
| Grams per 1,000 Seeds | 31.9 gm |
| 10. Disease Resistance | |
| Cucumber Scab (Gumosis) (*Cladosporium cucumerinum*) | Resistant |
| Cucumis Mosaic Virus (CMV) | Resistant |
| Powdery Mildew (*Sphaerotheca fuliginea*) | Resistant |
| Downy Mildew (*Pseudoperonospora cubensis*) | Resistant |
| Angular Leaf Spot (*Pseudomonas lachrymans*) | Resistant |
| Anthracnose (Race 1) (*Colletotrichum lagenaria*) | Resistant |

*These are typical values. Values may vary due to environment. Other values that are substantially equivalent are within the scope of the invention.

Inbred cucumber line APD147-5002Gy is a parthenocarpic pickling cucumber with superior characteristics, and provides an excellent pollen parent line and seed parent line in crosses for producing first generation (F1) hybrid cucumbers. It is an inbred line with high yield potential, has a vigorous indeterminate vine and dark green fruits with cylindrical shape and blunt ends, and exhibits parthenocarpy, and resistance to Anthracnose, Angular leaf spot, Scab, Powdery Mildew and Cucumber Mosaic Virus. The inbred line has shown uniformity and stability for the traits mentioned above, within the limits of environmental influence for the traits. It has been self pollinated several times with careful attention to uniformity of plant and fruit type. The line has been increased with continued observation for uniformity.

Pickling cucumbers grown in the North America have traditionally been gynoecious (i.e. not parthenocarpic) cucumber hybrids blended with a Monoecious hybrid as a blender, hence most of the product derived are pollinated fruits. The invention relates to an inbred line that is parthenocarpic with resistance to bacterial, fungal and viral pathogens and is similar to an American pickling cucumber in appearance. The new inbred incorporates the fruit quality and disease resistance found in an American pickling cucumber with few spines, and parthenocarpy from a European source.

Inbred cucumber line APD147-5002Gy is well adapted to US regions where pickling cucumbers are usually grown, including Michigan, Wisconsin, North Carolina, South Carolina, Georgia, Texas, Florida, and Missouri, as well as in Mexico, Central and South America and Asia. Inbred cucumber line APD147-5002Gy is resistant to Angular leaf spot (*Pseudomonas lachrymans*), Anthracnose race 1 (*Colletotrichum orbiculare*), Cucumber Scab (*Cladosporium cucumerinum*), Powdery Mildew (*Sphaerotheca fuliginea*) and Cucumber Mosaic Virus. Inbred cucumber line APD147-5002Gy has high yield potential, and has a vigorous indeterminate vine, and dark green fruits. It produces fruits with a round cross section, dark green skin color, small seed cavity, good blocky cylindrical shape with blunt ends at the stem end and blossom scar end. Hybrids made using APD147-5002Gy as a parent have shown good performance in terms of fruit quality, yield and disease resistance in North America, Mexico, Central America, Asia and South America.

Line APD147-5002Gy has been self-pollinated and planted for a number of generations to produce the homozygosity and phenotypic stability to make this line useful in commercial seed production. No variant traits have been observed or are expected for this line. Cucumber line APD147-5002Gy, being substantially homozygous, can be reproduced by planting seeds of the line, growing the resulting cucumber plant under self-pollinating or sib-pollinating conditions and harvesting the resulting seeds using techniques familiar to one of skill in the art.

C. Breeding Cucumber Line APD147-5002Gy

One aspect of the current invention concerns methods for crossing the cucumber line APD147-5002Gy with itself or a second plant and the seeds and plants produced by such methods. These methods can be used for propagation of line APD147-5002Gy, or can be used to produce hybrid cucumber seeds and the plants grown therefrom. Hybrid seeds are produced by crossing line APD147-5002Gy with second cucumber parent line.

The development of new varieties using one or more starting varieties is well known in the art. In accordance with the invention, novel varieties may be created by crossing line APD147-5002Gy followed by multiple generations of breeding according to such well known methods. New varieties may be created by crossing with any second plant. In selecting such a second plant to cross for the purpose of developing novel lines, it may be desired to choose those plants which either themselves exhibit one or more selected desirable characteristics or which exhibit the desired characteristic(s) in progeny. Once initial crosses have been made, inbreeding and selection take place to produce new varieties. For development of a uniform line, often five or more generations of selfing and selection are involved.

Uniform lines of new varieties may also be developed by way of double-haploids. This technique allows the creation of true breeding lines without the need for multiple generations of selfing and selection. In this manner, true breeding lines can be produced in as little as one generation. Haploid embryos may be produced from microspores, pollen, anther cultures, or ovary cultures. The haploid embryos may then be doubled autonomously, or by chemical treatments (e.g. colchicine treatment). Alternatively, haploid embryos may be grown into haploid plants and treated to induce chromosome doubling. In either case, fertile homozygous plants are obtained. In accordance with the invention, any of such techniques may be used in connection with line APD147-5002Gy and progeny thereof to achieve a homozygous line.

New varieties may be created, for example, by crossing line APD147-5002Gy with any second plant and selection of progeny in various generations and/or by doubled haploid technology. In choosing a second plant to cross for the purpose of developing novel lines, it may be desired to choose those plants which either themselves exhibit one or more selected desirable characteristics or which exhibit the desired characteristic(s) in progeny. After one or more lines are crossed, true-breeding lines may be developed.

Backcrossing can also be used to improve an inbred plant. Backcrossing transfers a specific desirable trait from one inbred or non-inbred source to an inbred that lacks that trait. This can be accomplished, for example, by first crossing a superior inbred (A) (recurrent parent) to a donor inbred (non-recurrent parent), which carries the appropriate locus or loci for the trait in question. The progeny of this cross are then mated back to the superior recurrent parent (A) followed by selection in the resultant progeny for the desired trait to be transferred from the non-recurrent parent. After five or more backcross generations with selection for the desired trait, the progeny are heterozygous for loci controlling the characteristic being transferred, but are like the superior parent for most or almost all other loci. The last backcross generation would be selfed to give pure breeding progeny for the trait being transferred.

The line of the present invention is particularly well suited for the development of new lines based on the elite nature of the genetic background of the line. In selecting a second plant to cross with APD147-5002Gy for the purpose of developing novel cucumber lines, it will typically be preferred to choose those plants which either themselves exhibit one or more selected desirable characteristics or which exhibit the desired characteristic(s) when in hybrid combination. Examples of desirable characteristics may include, but are not limited to, resistance to one or more viruses (e.g. cucumber mosaic virus, watermelon mosaic virus-II, cucumber necrosis virus, and cucumber vein yellowing ipomovirus, CYSDV), one or more fungi (e.g. anthracnose, caused by *Colletotrichum orbiculare*, downy mildew, caused by *Pseudoperonospora cubensis*, gummy stem blight caused by *Didymella bryoniae*, and powdery mildew, caused by *Oidium* sp. or *Erwinia* sp.), one or more bacteria (e.g. angular leaf spot, caused by *Pseudomonas syringae* pv. *lachrymans*, and bacterial wilt, caused by *Erwinia tracheiphila*, phytopthera caused by *Phytopthera infestans*), and one or more insects (e.g. the seedcorn maggot, *Delia platura*, the striped cucumber beetle, *Acalymma vittatum* (Fabricius), and the spotted cucumber beetle, *Diabrotica undecimpunctata howardi* (Barber). Non-limiting examples of genes that may be utilized for generating transgenic cucumber include RAR1 disease resistance proteins, as described in, for example, U.S. Pat. No. 7,098,378; the ability to tolerate high salt conditions, as described in, for example, U.S. Pat. Nos. 7,041,875 or 6,936,750; trehalose synthase for increased amounts of trehalose to increase tolerance to a variety of stresses, in particular to decreased availability of water, as described in, for example, U.S. Pat. No. 5,792,921; overexpression of phytochrome, such as for increased shade tolerance and/or darker green color, as described in, for example, U.S. Pat. No. 5,268,526; expression of reversibly glycosylated protein (RGP) for at least altered growth rates, as described in, for example, U.S. Pat. No. 6,194,638; improved growth under low-light conditions, such as with COP1, as described in, for example, U.S. Pat. No. 7,081,363 and so forth.

Examples of desirable characteristics related to the skin of the cucumber fruit include: a certain coloring, striping, and texture. Desirable characteristics related to the flesh of the cucumber fruit include: a certain flavor, taste, texture, thickness, color, sugar content, and solids content (% dry matter). Small or nonexistent seeds is another desired trait for cucumbers. Other desirable characteristics related to the fruit include: a certain fruit size and shape. Particularly desirable traits include: high fruit yield, early maturity, improved seed germination, and high seed yield. Desirable characteristics related to the environment include: tolerance to environmental stress (e.g. frost, drought, etc.) and adaptability to a wide variety of environmental conditions (e.g. soil acidity and salinity, temperature, and moisture).

D. Performance Characteristics

As described above, line APD147-5002Gy exhibits desirable agronomic traits, including resistance to Angular leaf spot (*Pseudomonas lachrymans*, also known as *Pseudomonas syringae* pv. *lachrymans*), Anthracnose race 1 (*Colletotrichum orbiculare*), Cucumber Scab (*Cladosporium cucumerinum*), Downy mildew (*Pseudopernospora cubensis*), Powdery Mildew (*Sphaerotheca fuliginea*) and Cucumber Mosaic Virus. The fruits of APD147-5002 Gy have a similar fruit shape, color, spines to a seeded American pickling cucumber.

As shown above, line APD147-5002Gy exhibits superior traits when compared to competing lines. One important aspect of the invention thus provides seed of the variety for commercial use. Such seed may be inbred or produced by crossing with any other, distinct plant. In certain, non-limiting examples, when line APD147-5002Gy was used as a parent in combination with other parthenocarpic cucumber inbred lines, the resulting hybrids were all Gy (all female flowers) and parthenocarpic. When APD147-5002Gy was used as a parent in combination with an inbred line which was monoecious, the resulting hybrids were Gy or predominantly female (majority female flowers in hybrid). When APD147-5002Gy was used as a parent in combination with a Gy inbred line the resulting hybrid was either Gy or predominantly female with or without parthenocarpy.

E. Further Embodiments of the Invention

When the term cucumber line APD147-5002Gy is used in the context of the present invention, this also includes plants modified to include at least a first desired heritable trait. Such plants may, in one embodiment, be developed by a plant breeding technique called backcrossing, wherein essentially all of the desired morphological and physiological characteristics of a variety are recovered in addition to a genetic locus transferred into the plant via the backcrossing technique. The term single locus converted plant as used herein refers to those cucumber plants which are developed by a plant breeding technique called backcrossing, wherein essentially all of the desired morphological and physiological characteristics of a variety are recovered in addition to the single locus transferred into the variety via the backcrossing technique.

Backcrossing methods can be used with the present invention to improve or introduce a characteristic into the present variety. The parental cucumber plant which contributes the locus for the desired characteristic is termed the nonrecurrent or donor parent. This terminology refers to the fact that the nonrecurrent parent is used one time in the backcross protocol and therefore does not recur. The parental cucumber plant to which the locus or loci from the nonrecurrent parent are transferred is known as the recurrent parent as it is used for several rounds in the backcrossing protocol.

In a typical backcross protocol, the original variety of interest (recurrent parent) is crossed to a second variety (nonrecurrent parent) that carries the single locus of interest to be transferred. The resulting progeny from this cross are then crossed again to the recurrent parent and the process is repeated until a cucumber plant is obtained wherein essentially all of the desired morphological and physiological characteristics of the recurrent parent are recovered in the converted plant, in addition to the single transferred locus from the nonrecurrent parent.

The selection of a suitable recurrent parent is an important step for a successful backcrossing procedure. The goal of a backcross protocol is to alter or substitute a single trait or characteristic in the original variety. To accomplish this, a single locus of the recurrent variety is modified or substituted with the desired locus from the nonrecurrent parent, while retaining essentially all of the rest of the desired genetic, and therefore the desired physiological and morphological constitution of the original variety. The choice of the particular nonrecurrent parent will depend on the purpose of the backcross; one of the major purposes is to add some commercially desirable trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred.

In one embodiment, progeny cucumber plants of a backcross in which APD147-5002Gy is the recurrent parent comprise (i) the desired trait from the non-recurrent parent and (ii) all of the physiological and morphological characteristics of cucumber line APD147-5002Gy as determined at the 5% significance level when grown in the same environmental conditions.

Cucumber varieties can also be developed from more than two parents. The technique, known as modified backcrossing, uses different recurrent parents during the backcrossing. Modified backcrossing may be used to replace the original recurrent parent with a variety having certain more desirable characteristics or multiple parents may be used to obtain different desirable characteristics from each.

Many single locus traits have been identified that are not regularly selected for in the development of a new inbred but that can be improved by backcrossing techniques. Single locus traits may or may not be transgenic; examples of these traits include, but are not limited to, male sterility, herbicide resistance, resistance to bacterial, fungal, or viral disease, insect resistance, restoration of male fertility, modified fatty acid or carbohydrate metabolism, and enhanced nutritional quality. These comprise genes generally inherited through the nucleus.

Direct selection may be applied where the single locus acts as a dominant trait. An example of a dominant trait is the anthracnose resistance trait. For this selection process, the progeny of the initial cross are sprayed with anthracnose spores prior to the backcrossing. The spraying eliminates any plants which do not have the desired anthracnose resistance characteristic, and only those plants which have the anthracnose resistance gene are used in the subsequent backcross. This process is then repeated for all additional backcross generations.

Selection of cucumber plants for breeding is not necessarily dependent on the phenotype of a plant and instead can be based on genetic investigations. For example, one can utilize a suitable genetic marker which is closely genetically linked to a trait of interest. One of these markers can be used to identify the presence or absence of a trait in the offspring of a particular cross, and can be used in selection of progeny for continued breeding. This technique is commonly referred to as marker assisted selection. Any other type of genetic marker or other assay which is able to identify the relative presence or absence of a trait of interest in a plant can also be useful for breeding purposes.

Procedures for marker assisted selection applicable to the breeding of cucumber are well known in the art. Such methods will be of particular utility in the case of recessive traits and variable phenotypes, or where conventional assays may be more expensive, time consuming or otherwise disadvantageous. Types of genetic markers which could be used in accordance with the invention include, but are not necessarily limited to, Simple Sequence Length Polymorphisms (SSLPs) (Williams et al., 1990), Randomly Amplified Polymorphic DNAs (RAPDs), DNA Amplification Fingerprinting (DAF), Sequence Characterized Amplified Regions (SCARs), Arbitrary Primed Polymerase Chain Reaction (AP-PCR), Amplified Fragment Length Polymorphisms (AFLPs) (EP 534 858, specifically incorporated herein by reference in its entirety), and Single Nucleotide Polymorphisms (SNPs) (Wang et al., 1998).

The invention further provides methods for developing cucumber plants in a cucumber plant breeding program using plant breeding techniques including recurrent selection, backcrossing, pedigree breeding, restriction fragment length polymorphism enhanced selection, genetic marker enhanced selection and transformation. Marker loci such as restriction fragment polymorphisms or random amplified DNA have been published for many years and may be used for selection (See Pierce et al., 1990; Wehner, 1997; and Kennard et al., 1994). Seeds, cucumber plants, and parties thereof produced by such breeding methods are also part of the invention.

F. Plants Derived from Cucumber Line APD147-5002Gy by Genetic Engineering

Many useful traits that can be introduced by backcrossing, as well as directly into a plant, are those which are introduced by genetic transformation techniques. Genetic transformation may therefore be used to insert a selected transgene into the cucumber line of the invention or may, alternatively, be used for the preparation of transgenes which can be introduced by backcrossing. Methods for the transformation of plants, including cucumber, are well known to those of skill in the art. Techniques which may be employed for the genetic transformation of cucumber include, but are not limited to, electroporation, microprojectile bombardment, *Agrobacterium*-mediated transformation and direct DNA uptake by protoplasts.

To effect transformation by electroporation, one may employ either friable tissues, such as a suspension culture of cells or embryogenic callus or alternatively one may transform immature embryos or other organized tissue directly. In this technique, one would partially degrade the cell walls of the chosen cells by exposing them to pectin-degrading enzymes (pectolyases) or mechanically wound tissues in a controlled manner.

A particularly efficient method for delivering transforming DNA segments to plant cells is microprojectile bombardment. In this method, particles are coated with nucleic acids and delivered into cells by a propelling force. Exemplary particles include those comprised of tungsten, platinum, and preferably, gold. For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate.

An illustrative embodiment of a method for delivering DNA into plant cells by acceleration is the Biolistics Particle Delivery System, which can be used to propel particles coated with DNA or cells through a screen, such as a stainless steel or Nytex screen, onto a surface covered with target cucumber cells. The screen disperses the particles so that they are not delivered to the recipient cells in large aggregates. It is believed that a screen intervening between the projectile apparatus and the cells to be bombarded reduces the size of projectiles aggregate and may contribute to a higher frequency of transformation by reducing the damage inflicted on the recipient cells by projectiles that are too large.

Microprojectile bombardment techniques are widely applicable, and may be used to transform virtually any plant species.

Agrobacterium-mediated transformation of cucumber explant material and regeneration of whole transformed cucumber plants has been shown to be an efficient transformation method (U.S. Pat. No. 6,084,152). An advantage of the technique is that DNA can be introduced into whole plant tissues, thereby bypassing the need for regeneration of an intact plant from a protoplast. Modern Agrobacterium transformation vectors are capable of replication in E. coli as well as Agrobacterium, allowing for convenient manipulations (Klee et al., 1985). Moreover, recent technological advances in vectors for Agrobacterium-mediated gene transfer have improved the arrangement of genes and restriction sites in the vectors to facilitate the construction of vectors capable of expressing various polypeptide coding genes. The vectors described have convenient multi-linker regions flanked by a promoter and a polyadenylation site for direct expression of inserted polypeptide coding genes. Additionally, Agrobacterium containing both armed and disarmed Ti genes can be used for transformation.

In those plant strains where Agrobacterium-mediated transformation is efficient, it is the method of choice because of the facile and defined nature of the gene locus transfer. The use of Agrobacterium-mediated plant integrating vectors to introduce DNA into plant cells is well known in the art (Fraley et al., 1985; U.S. Pat. No. 5,563,055).

Transformation of plant protoplasts also can be achieved using methods based on calcium phosphate precipitation, polyethylene glycol treatment, electroporation, and combinations of these treatments (see, e.g., Potrykus et al., 1985; Omirulleh et al., 1993; Fromm et al., 1986; Uchimiya et al., 1986; Marcotte et al., 1988). Transformation of plants and expression of foreign genetic elements is exemplified in Choi et al. (1994), and Ellul et al. (2003).

A number of promoters have utility for plant gene expression for any gene of interest including but not limited to selectable markers, scoreable markers, genes for pest tolerance, disease resistance, nutritional enhancements and any other gene of agronomic interest. Examples of constitutive promoters useful for cucumber plant gene expression include, but are not limited to, the cauliflower mosaic virus (CaMV) P-35S promoter, which confers constitutive, high-level expression in most plant tissues (see, e.g., Odel et al., 1985), including monocots (see, e.g., Dekeyser et al., 1990; Terada and Shimamoto, 1990); a tandemly duplicated version of the CaMV 35S promoter, the enhanced 35S promoter (P-e35S) the nopaline synthase promoter (An et al., 1988), the octopine synthase promoter (Fromm et al., 1989); and the figwort mosaic virus (P-FMV) promoter as described in U.S. Pat. No. 5,378,619 and an enhanced version of the FMV promoter (P-eFMV) where the promoter sequence of P-FMV is duplicated in tandem, the cauliflower mosaic virus 19S promoter, a sugarcane bacilliform virus promoter, a commelina yellow mottle virus promoter, and other plant DNA virus promoters known to express in plant cells.

A variety of plant gene promoters that are regulated in response to environmental, hormonal, chemical, and/or developmental signals can be used for expression of an operably linked gene in plant cells, including promoters regulated by (1) heat (Callis et al., 1988), (2) light (e.g., pea rbcS-3A promoter, Kuhlemeier et al., 1989; maize rbcS promoter, Schaffner and Sheen, 1991; or chlorophyll a/b-binding protein promoter, Simpson et al., 1985), (3) hormones, such as abscisic acid (Marcotte et al., 1989), (4) wounding (e.g., wun1, Siebertz et al., 1989); or (5) chemicals such as methyl jasmonate, salicylic acid, or a safener. It may also be advantageous to employ organ-specific promoters (e.g., Roshal et al., 1987; Schemthaner et al., 1988; Bustos et al., 1989).

Exemplary nucleic acids which may be introduced to the cucumber lines of this invention include, for example, DNA sequences or genes from another species, or even genes or sequences which originate with or are present in the same species, but are incorporated into recipient cells by genetic engineering methods rather than classical reproduction or breeding techniques. However, the term "exogenous" is also intended to refer to genes that are not normally present in the cell being transformed, or perhaps simply not present in the form, structure, etc., as found in the transforming DNA segment or gene, or genes which are normally present and that one desires to express in a manner that differs from the natural expression pattern, e.g., to over-express. Thus, the term "exogenous" gene or DNA is intended to refer to any gene or DNA segment that is introduced into a recipient cell, regardless of whether a similar gene may already be present in such a cell. The type of DNA included in the exogenous DNA can include DNA which is already present in the plant cell, DNA from another plant, DNA from a different organism, or a DNA generated externally, such as a DNA sequence containing an antisense message of a gene, or a DNA sequence encoding a synthetic or modified version of a gene.

Many hundreds if not thousands of different genes are known and could potentially be introduced into a cucumber plant according to the invention. Non-limiting examples of particular genes and corresponding phenotypes one may choose to introduce into a cucumber plant include one or more genes for insect tolerance, such as a Bacillus thuringiensis (B.t.) gene, pest tolerance such as genes for fungal disease control, herbicide tolerance such as genes conferring glyphosate tolerance, and genes for quality improvements such as yield, nutritional enhancements, environmental or stress tolerances, or any desirable changes in plant physiology, growth, development, morphology or plant product(s). For example, structural genes would include any gene that confers insect tolerance including but not limited to a Bacillus insect control protein gene as described in WO 99/31248, herein incorporated by reference in its entirety, U.S. Pat. No. 5,689,052, herein incorporated by reference in its entirety, U.S. Pat. Nos. 5,500,365 and 5,880,275, herein incorporated by reference it their entirety. In another embodiment, the structural gene can confer tolerance to the herbicide glyphosate as conferred by genes including, but not limited to *Agrobacterium* strain CP4 glyphosate resistant EPSPS gene (aroA:CP4) as described in U.S. Pat. No. 5,633,435, herein incorporated by reference in its entirety, or glyphosate oxidoreductase gene (GOX) as described in U.S. Pat. No. 5,463,175, herein incorporated by reference in its entirety.

Alternatively, the DNA coding sequences can affect these phenotypes by encoding a non-translatable RNA molecule that causes the targeted inhibition of expression of an endogenous gene, for example via antisense- or cosuppression-mediated mechanisms (see, for example, Bird et al., 1991). The RNA could also be a catalytic RNA molecule (i.e., a ribozyme) engineered to cleave a desired endogenous mRNA product (see for example, Gibson and Shillito, 1997). Thus, any gene which produces a protein or mRNA which expresses a phenotype or morphology change of interest is useful for the practice of the present invention.

G. Definitions

In the description and tables herein, a number of terms are used. In order to provide a clear and consistent understanding of the specification and claims, the following definitions are provided:

A: When used in conjunction with the word "comprising" or other open language in the claims, the words "a" and "an" denote "one or more."

Allele: Any of one or more alternative forms of a gene locus, all of which alleles relate to one trait or characteristic. In a diploid cell or organism, the two alleles of a given gene occupy corresponding loci on a pair of homologous chromosomes.

Backcrossing: A process in which a breeder repeatedly crosses hybrid progeny, for example a first generation hybrid ($F_1$), back to one of the parents of the hybrid progeny. Backcrossing can be used to introduce one or more single locus conversions from one genetic background into another.

Crossing: The mating of two parent plants.

Cross-pollination: Fertilization by the union of two gametes from different plants.

Diploid: A cell or organism having two sets of chromosomes.

Emasculate: The removal of plant male sex organs or the inactivation of the organs with a cytoplasmic or nuclear genetic factor conferring male sterility or a chemical agent.

Enzymes: Molecules which can act as catalysts in biological reactions.

$F_1$ Hybrid: The first generation progeny of the cross of two nonisogenic plants.

Genotype: The genetic constitution of a cell or organism.

Haploid: A cell or organism having one set of the two sets of chromosomes in a diploid.

Linkage: A phenomenon wherein alleles on the same chromosome tend to segregate together more often than expected by chance if their transmission was independent.

Marker: A readily detectable phenotype, preferably inherited in codominant fashion (both alleles at a locus in a diploid heterozygote are readily detectable), with no environmental variance component, i.e., heritability of 1.

Phenotype: The detectable characteristics of a cell or organism, which characteristics are the manifestation of gene expression.

Quantitative Trait Loci (QTL): Quantitative trait loci (QTL) refer to genetic loci that control to some degree numerically representable traits that are usually continuously distributed.

Regeneration: The development of a plant from tissue culture.

Self-pollination: The transfer of pollen from the anther to the stigma of the same plant.

Single Locus Converted (Conversion) Plant: Plants which are developed by a plant breeding technique called backcrossing, wherein essentially all of the desired morphological and physiological characteristics of a cucumber variety are recovered in addition to the characteristics of the single locus transferred into the variety via the backcrossing technique and/or by genetic transformation.

Substantially Equivalent: A characteristic that, when compared, does not show a statistically significant difference (e.g., p=0.05) from the mean.

Tetraploid: A cell or organism having four sets of chromosomes.

Tissue Culture: A composition comprising isolated cells of the same or a different type or a collection of such cells organized into parts of a plant.

Transgene: A genetic locus comprising a sequence which has been introduced into the genome of a cucumber plant by transformation.

Triploid: A cell or organism having three sets of chromosomes.

H. Deposit Information

A deposit of cucumber line APD147-5002Gy, disclosed above and recited in the claims, has been made with the American Type Culture Collection (ATCC), 10801 University Blvd., Manassas, Va. 20110-2209. The date of deposit was Dec. 27, 2006. Upon issuance of a patent, all restrictions upon the deposit will be removed, and the deposit is intended to meet all of the requirements of 37 C.F.R. §1.801-1.809. The accession number for those deposited seeds of cucumber line APD147-5002Gy is ATCC Accession No. PTA-8104. The deposit will be maintained in the depository for a period of 30 years, or 5 years after the last request, or for the effective life of the patent, whichever is longer, and will be replaced if necessary during that period.

Although the foregoing invention has been described in some detail by way of illustration and example for purposes of clarity and understanding, it will be obvious that certain changes and modifications may be practiced within the scope of the invention, as limited only by the scope of the appended claims.

All references cited herein are hereby expressly incorporated herein by reference.

REFERENCES

The following references, to the extent that they provide exemplary procedural or other details supplementary to those set forth herein, are specifically incorporated herein by reference:

U.S. Pat. No. 4,822,949
U.S. Pat. No. 5,268,526
U.S. Pat. No. 5,349,128
U.S. Pat. No. 5,378,619
U.S. Pat. No. 5,463,175
U.S. Pat. No. 5,492,827
U.S. Pat. No. 5,500,365
U.S. Pat. No. 5,563,055
U.S. Pat. No. 5,623,066
U.S. Pat. No. 5,633,435
U.S. Pat. No. 5,689,052
U.S. Pat. No. 5,792,921
U.S. Pat. No. 5,880,275
U.S. Pat. No. 6,015,942
U.S. Pat. No. 6,084,152

U.S. Pat. No. 6,127,601
U.S. Pat. No. 6,194,638
U.S. Pat. No. 6,342,655
U.S. Pat. No. 6,765,130
U.S. Pat. No. 6,936,750
U.S. Pat. No. 7,041,875
U.S. Pat. No. 7,081,363
U.S. Pat. No. 7,098,378
An et al., *Plant Physiol.,* 88:547, 1988.
Bird et al., *Biotech. Gen. Engin. Rev.,* 9:207, 1991.
Bustos et al., *Plant Cell,* 1:839, 1989.
Callis et al., *Plant Physiol.,* 88:965, 1988.
Choi et al., *Plant Cell Rep.,* 13: 344-348, 1994.
Dekeyser et al., *Plant Cell,* 2:591, 1990.
Ellul et al., *Theor. Appl. Genet.,* 107:462-469, 2003.
EP 534 858
Fraley et al., *Bio/Technology,* 3:629-635, 1985.
Fromm et al., *Nature,* 312:791-793, 1986.
Fromm et al., *Plant Cell,* 1:977, 1989.
Gibson and Shillito, *Mol. Biotech.,* 7:125, 1997
Kennard et al., *Theoretical Applied Genetics* 89:217-224, 1994.
Klee et al., *Bio-Technology,* 3:637-642, 1985.
Kuhlemeier et al., *Plant Cell,* 1:471, 1989.
Marcotte et al., *Nature,* 335:454, 1988.
Marcotte et al., *Plant Cell,* 1:969, 1989.
Odel et al., *Nature,* 313:810, 1985.
Omirulleh et al., *Plant Mol. Biol.,* 21:415-428, 1993.
PCT Appln. WO 99/31248
Pierce et al., *HortScience* 25:605-615, 1990.
Potrykus et al., *Mol. Gen. Genet.,* 199:183-188, 1985.
Roshal et al., *EMBO J.,* 6:1155, 1987.
Sarreb et al., In: *Comparison of triploid and diploid cucumber in long-term liquid cultures,* Springer, 71:231-235, 2002.
Schaffner and Sheen, *Plant Cell,* 3:997, 1991.
Schernthaner et al., *EMBO J.,* 7:1249, 1988.
Siebertz et al., *Plant Cell,* 1:961, 1989.
Simpson et al., *EMBO J.,* 4:2723, 1985.
Terada and Shimamoto, *Mol. Gen. Genet.,* 220:389, 1990.
Uchimiya et al., *Mol. Gen. Genet.,* 204:204, 1986.
Wang et al., *Science,* 280:1077-1082, 1998.
Wehner T., *Cucurbit Genetics Cooperative Report,* 20:66-68, 1997
Williams et al., *Nucleic Acids Res.,* 18:6531-6535, 1990.

What is claimed is:

1. A seed of a cucumber line APD147-5002Gy, wherein a sample of the seed of cucumber line APD147-5002Gy was deposited under ATCC Accession Number PTA-8104.

2. A plant of cucumber line APD147-5002Gy, wherein a sample of the seed of cucumber line APD147-5002Gy was deposited under ATCC Accession Number PTA-8104.

3. A plant part of the plant of claim 2.

4. The plant part of claim 3, wherein said part is selected from the group consisting of a leaf, fruit, pollen, an ovule and a cell.

5. A cucumber plant, or a part thereof, having all the physiological and morphological characteristics of the cucumber plant of claim 2.

6. A tissue culture of regenerable cells of cucumber line APD147-5002Gy, wherein a sample of the seed of cucumber line APD147-5002Gy was deposited under ATCC Accession Number PTA-8104.

7. The tissue culture according to claim 6, comprising cells or protoplasts from a plant part selected from the group consisting of embryos, meristems, cotyledons, pollen, leaves, anthers, roots, root tips, pistil, flower, seed and stalks.

8. A cucumber plant regenerated from the tissue culture of claim 6, wherein the regenerated plant expresses all of the physiological and morphological characteristics of cucumber line APD147-5002Gy, wherein a sample of the seed of cucumber line APD147-5002Gy was deposited under ATCC Accession Number PTA-8104.

9. A method of producing cucumber seed, said method comprising crossing a plant of cucumber line APD147-5002Gy with a second cucumber plant, wherein a sample of the seed of cucumber line APD147-5002Gy was deposited under ATCC Accession Number PTA-8104.

10. The method of claim 9, wherein the plant of cucumber line APD147-5002Gy is the female parent.

11. The method of claim 9, wherein the plant of cucumber line APD147-5002Gy is the male parent.

12. An F1 hybrid seed produced by the method of claim 9.

13. An F1 hybrid plant produced by growing the seed of claim 12.

14. A method for producing a seed of a line APD147-5002Gy-derived cucumber plant, said method comprising the steps of:
   (a) crossing a cucumber plant of line APD147-5002Gy with a second cucumber plant, wherein a sample of the seed of cucumber line APD147-5002Gy was deposited under ATCC Accession Number PTA-8104; and
   (b) allowing seed of a APD147-5002Gy-derived cucumber plant to form.

15. The method of claim 14, further comprising the steps of:
   (c) crossing a plant grown from said APD147-5002Gy-derived cucumber seed with itself or a second cucumber plant to yield additional APD 147-5002Gy-derived cucumber seed;
   (d) growing said additional APD147-5002Gy-derived cucumber seed of step (c) to yield additional APD147-5002Gy-derived cucumber plants; and
   (e) repeating the crossing and growing steps of (c) and (d) to generate further APD147-5002Gy-derived cucumber plants.

16. A method of vegetatively propagating a plant of cucumber line APD147-5002Gy, said method comprising the steps of:
   (a) collecting tissue capable of being propagated from a cucumber plant of line APD147-5002Gy, wherein a sample of the seed of cucumber line APD147-5002Gy was deposited under ATCC Accession Number PTA-8104;
   (b) cultivating said tissue to obtain proliferated shoots; and
   (c) rooting said proliferated shoots to obtain rooted plantlets.

17. The method of claim 16, further comprising growing plants from said rooted plantlets.

18. A method of introducing a desired trait into cucumber line APD147-5002Gy, said method comprising:
   (a) crossing a plant of line APD147-5002Gy with a second cucumber plant that comprises a desired trait to produce F1 progeny, wherein a sample of the seed of cucumber line APD147-5002Gy was deposited under ATCC Accession Number PTA-8104;
   (b) selecting an F1 progeny that comprises the desired trait;
   (c) crossing the selected F1 progeny with a plant of line APD147-5002Gy to produce backcross progeny;
   (d) selecting backcross progeny comprising the desired trait and the physiological and morphological characteristic of cucumber line APD147-5002Gy; and
   (e) repeating steps (c) and (d) three or more times in succession to produce selected fourth or higher backcross progeny that comprise the desired trait and all of the physiological and morphological characteristics of cucumber line APD147-5002Gy when grown in the same environmental conditions.

19. A cucumber plant produced by the method of claim 18.

20. A method of producing a plant of cucumber line APD147-5002Gy comprising an added desired trait, the method comprising introducing a transgene conferring the desired trait into a plant of cucumber line APD147-5002Gy, wherein a sample of the seed of cucumber line APD147-5002Gy was deposited under ATCC Accession Number PTA-8104.

21. A progeny plant of the plant of claim 2 that comprises all of the physiological and morphological characteristics of cucumber line APD147-5002Gy, wherein a sample of the seed of cucumber line APD147-5002Gy was deposited under ATCC Accession Number PTA-8104.

22. A seed that produces the plant of claim 21.

23. A method of determining the genotype of a plant of cucumber line APD147-5002Gy, said method comprising obtaining a sample of nucleic acids from said plant and detecting in said nucleic acids a plurality of polymorphisms, wherein a sample of the seed of cucumber line APD147-5002Gy was deposited under ATCC Accession Number PTA-8104.

24. The method of claim 23, further comprising storing the results of detecting the plurality of polymorphisms on a computer readable medium.

25. A method of producing cucumber, said method comprising:
(a) cultivating the plant of claim 2 to maturity, and
(b) obtaining at least a first cucumber from the plant.

* * * * *